US012667293B2

(12) United States Patent
Matsumaru

(10) Patent No.: US 12,667,293 B2
(45) Date of Patent: Jun. 30, 2026

(54) APPARATUS USED TO DETECT OR STIMULATE ACTIVITY OF NERVE TISSUE

(71) Applicants: Epsilon Medical Inc., Tokyo (JP); UNIVERSITY OF TSUKUBA, Ibaraki (JP)

(72) Inventor: Yuji Matsumaru, Tsukuba (JP)

(73) Assignees: Epsilon Medical Inc., Tokyo (JP); UNIVERSITY OF TSUKUBA, Ibaraki (JP)

( * ) Notice: Subject to any disclaimer, the term of this patent is extended or adjusted under 35 U.S.C. 154(b) by 321 days.

(21) Appl. No.: 18/264,182

(22) PCT Filed: Jan. 17, 2022

(86) PCT No.: PCT/JP2022/001367
§ 371 (c)(1),
(2) Date: Aug. 3, 2023

(87) PCT Pub. No.: WO2022/172694
PCT Pub. Date: Aug. 18, 2022

(65) Prior Publication Data
US 2024/0099631 A1     Mar. 28, 2024

(30) Foreign Application Priority Data

Feb. 9, 2021     (JP) ................................. 2021-018995

(51) Int. Cl.
*A61B 5/293* (2021.01)
*A61B 5/00* (2006.01)
*A61N 1/05* (2006.01)

(52) U.S. Cl.
CPC ............ *A61B 5/293* (2021.01); *A61B 5/6868* (2013.01); *A61B 5/6876* (2013.01);
(Continued)

(58) Field of Classification Search
CPC ..... A61B 5/293; A61B 5/6868; A61B 5/6876; A61N 1/3605; A61N 1/0529; A61N 1/3714; A61N 1/37516
See application file for complete search history.

(56) References Cited

U.S. PATENT DOCUMENTS

| | | | | |
|---|---|---|---|---|
| 5,549,109 A | * | 8/1996 | Samson | A61B 5/6851 600/585 |
| 6,757,970 B1 | * | 7/2004 | Kuzma | A61N 1/0551 600/374 |

(Continued)

FOREIGN PATENT DOCUMENTS

| | | |
|---|---|---|
| JP | 2007-111118 A | 5/2007 |
| JP | 2013-236662 A | 11/2013 |

(Continued)

OTHER PUBLICATIONS

Gerboni G. et al., "Cortical Brain Stimulation with Endovascular Electrodes", 2018 40th Annual International Conference of the IEEE Engineering in Medicine and Biology Society (EMBC), IEEE, Jul. 18, 2018, pp. 3088-3091, XP033429019.

(Continued)

*Primary Examiner* — Eun Hwa Kim
(74) *Attorney, Agent, or Firm* — Studebaker Brackett PLLC

(57)     ABSTRACT

This apparatus (1) comprises at least one intravascular device (10), (20) that is disposed in a blood vessel of an organism and that is equipped with at least one electrode (11), (12), (21), (22) for detecting or stimulating the activity of nerve tissue positioned outside the blood vessel nearby, the electrodes (11), (12), (21), (22) being provided on a wire member.

10 Claims, 5 Drawing Sheets

(52) U.S. Cl.
CPC .......... *A61B 5/6882* (2013.01); *A61N 1/0539* (2013.01); *A61B 2562/043* (2013.01)

(56) References Cited

U.S. PATENT DOCUMENTS

| | | | |
|---|---|---|---|
| 9,297,845 | B2 | 3/2016 | Mathur |
| 9,827,039 | B2 | 11/2017 | Dandler et al. |
| 2006/0074449 | A1 | 4/2006 | Denker et al. |
| 2010/0211131 | A1 | 8/2010 | Williams et al. |
| 2013/0116685 | A1 | 5/2013 | Deem et al. |
| 2014/0066949 | A1 | 3/2014 | Eskuri |
| 2015/0148645 | A1* | 5/2015 | Regnier ................. A61N 1/056 607/116 |
| 2016/0287325 | A1 | 10/2016 | Yamasaki et al. |
| 2017/0000560 | A1 | 1/2017 | Mathur et al. |
| 2022/0167924 | A1* | 6/2022 | Rapoport ............... A61B 5/293 |

FOREIGN PATENT DOCUMENTS

| | | |
|---|---|---|
| JP | 2016-123806 A | 7/2016 |
| JP | 2017-159079 A | 9/2017 |
| JP | 6204483 B2 | 9/2017 |
| JP | 2019-516512 A | 6/2019 |
| WO | 2015/049966 A1 | 4/2015 |
| WO | 2017/203380 A1 | 11/2017 |

OTHER PUBLICATIONS

The extended European search report issued by the European Patent Office on Jun. 10, 2024, which corresponds to European Patent Application No. 22752527.6-1122 and is related to U.S. Appl. No. 18/264,182.

An Office Action; "Notice of Reasons for Refusal," mailed by the Japanese Patent Office on Oct. 29, 2024, which corresponds to Japanese Patent Application No. 2021-018995 and is related to U.S. Appl. No. 18/264,182; with English language translation.

International Search Report issued in PCT/JP2022/001367; mailed Mar. 29, 2022.

Communication pursuant to Article 94(3) EPC issued by the European Patent Office on Feb. 12, 2025, which corresponds to European Patent Application No. 22752527.6-1122 and is related to U.S. Appl. No. 18/264,182.

* cited by examiner

FIG. 2
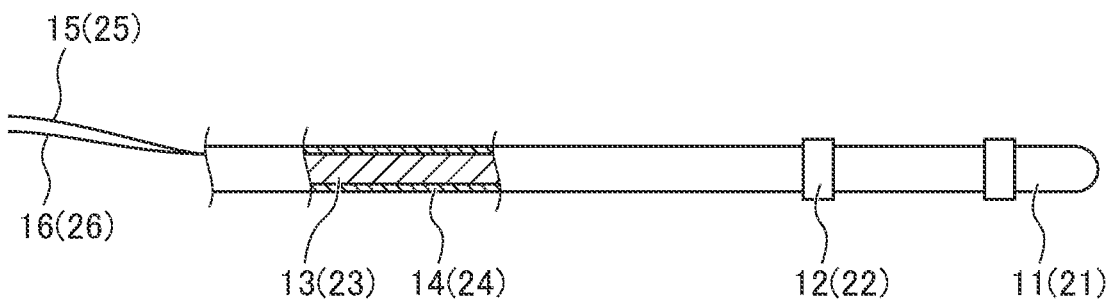
FIG. 3
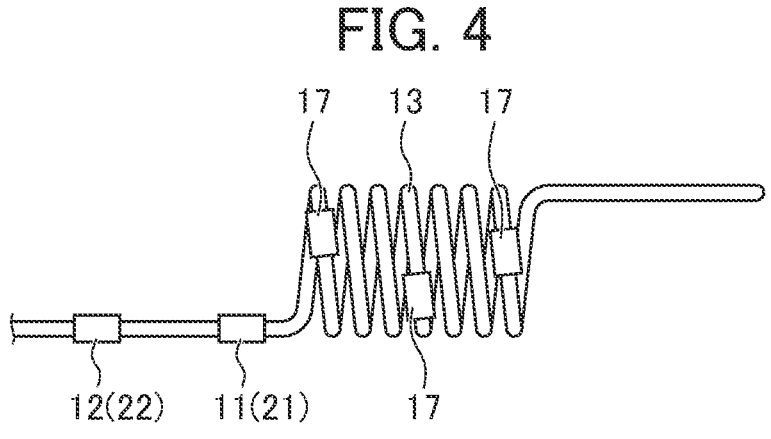
FIG. 4

START

DISPOSE FIRST INTRAVASCULAR DEVICE IN CEREBRAL BLOOD VESSEL. — S11

DISPOSE SECOND INTRAVASCULAR DEVICE IN CEREBRAL BLOOD VESSEL SPACED APART FROM FIRST INTRAVASCULAR DEVICE BY A PREDETERMINED DISTANCE. — S12

ATTACH FIRST REFERENCE ELECTRODE TO EARLOBE. — S13

ATTACH SECOND REFERENCE ELECTRODE TO EARLOBE. — S14

START MEASUREMENT. — S15

END MEASUREMENT. — S16

END

F3
F4
}
FRONTAL REGION
(COMPARATIVE EXAMPLE)

P3
P4
}
OCCIPITAL REGION
(COMPARATIVE EXAMPLE)

11
12
}
FRONTAL REGION
(PRESENT EMBODIMENT)

APPARATUS USED TO DETECT OR STIMULATE ACTIVITY OF NERVE TISSUE

TECHNICAL FIELD

The present invention relates to an apparatus used to detect or stimulate activity of nerve tissue.

BACKGROUND ART

Conventionally, when measuring the brain waves of organisms such as animals and humans, transcranial measurement in which electrodes are attached to the scalp have been performed. While such methods allow for convenient measurement of brain waves, they have the following flaws. Specifically, only information from the surface of the brain can be obtained, and thus only brain waves from the vicinity of the surface of the brain can be measured, and it is not possible to measure brain waves generated in the deeper portions of the brain. In addition, because brain waves are attenuated as they pass through the cranium, precise measurement is difficult.

Methods that address these flaws, such as subdural EEG and stereotactic EEG (SEEG), have begun to be employed recently. With these methods, the cranium is opened, or a hole is opened in the cranium, and electrodes are directly inserted into the brain to measure brain waves. Thus, although highly invasive, these methods enable measuring the necessary brain waves with high precision. SEEG also enables measuring of brain waves in the deep portions of the brain, making it possible to, for example, identify regions of brain tissue that cause epilepsy.

However, as mentioned above, subdural EEG and SEEG have a problem in that they necessitate opening of the cranium or the opening of a hole in the cranium, and thus are highly invasive. This requires procedures for opening the cranium or opening a hole in the cranium to be performed, making it impossible to perform measurement in a simple manner, and making it difficult to perform measuring over a long time, such as a few days or more. Further, SEEG is an extremely costly procedure.

Patent Document 1 discloses a technique for sensing or stimulating electric activity of nerve tissue in a blood vessel. Specifically, in Patent Document 1, a stent provided with an electrode is expanded in a cerebral blood vessel and retained against the blood vessel wall, whereby electric activity of nearby nerve tissue can be sensed or stimulated.

Patent Document 1: Japanese Unexamined Patent Application, Publication No. 2017-159079

DISCLOSURE OF THE INVENTION

Problems to be Solved by the Invention

However, the technique of Patent Document 1 uses a stent having an expansive force, and thus friction with the catheter during delivery to the cerebral blood vessel may cause a decrease in operability. The bulk of the electrode may further exacerbate this phenomenon. Moreover, the metal struts of the stent remain in contact with the cerebral blood vessel wall over a wide area, and therefore, prolonged use may increase the risk of blood clots.

The problem to be solved by the present invention is to provide an apparatus that is used for detecting or stimulating activity of nerve tissue, the apparatus being easily deliverable to a cerebral blood vessel and being able to reduce contact with the blood vessel wall.

Means for Solving the Problems

The present invention solves the above problem by the following solution. In order to facilitate understanding, numerals corresponding to an embodiment of the present invention are added in the below description, but the present invention is not so limited.

A first invention is an apparatus (1) including at least one intravascular device (10, 20) disposed in a blood vessel of an organism and including at least one electrode (11, 12, 21, 22) for detecting or stimulating activity of nerve tissue positioned outside the blood vessel nearby, wherein the electrode (11, 12, 21, 22) is provided on a wire member.

A second invention is the apparatus (1) according to the first invention, wherein at least one of the intravascular devices (10, 20) has a plurality of the electrodes (11, 12, 21, 22), the electrodes (11, 12, 21, 22) being provided on the same wire member and being spaced apart from each other by less than 1 cm.

A third invention is the apparatus (1) according to the first or the second invention, including a plurality of the intravascular devices (10, 20), wherein the electrodes (11, 12, 21, 22) of separate intravascular devices (10, 20) are disposed in the blood vessel and are spaced apart from each other by 1 cm or more.

A fourth invention is the apparatus (1) according to any one of the first to third inventions, wherein the wire member has a spiral portion (13) having a diameter that can expand and contract circumferentially so as to be retained against a wall of the blood vessel in an expanded state.

A fifth invention is the apparatus (1) according to any one of the first to fourth inventions, wherein the intravascular device (1) remains in the blood vessel for one day or longer.

A sixth invention is the apparatus (1) according to any one of the first to fifth inventions, wherein the blood vessel in which the intravascular device is disposed is a cerebral venous sinus.

Effects of the Invention

According to the present invention, it is possible to provide an apparatus that is used for detecting or stimulating activity of nerve tissue, the apparatus being easily deliverable to a cerebral blood vessel and having reduced contact with the blood vessel wall.

BRIEF DESCRIPTION OF THE DRAWINGS

FIG. 2 illustrates an example of a configuration of the vicinity of a tip on the side of a first intravascular device 10 to be inserted into a cerebral blood vessel;

FIG. 3 illustrates another example of the configuration of the vicinity of the tip on the side of the first intravascular device 10 to be inserted into a cerebral blood vessel;

FIG. 4 illustrates a variant of the first intravascular device 10 illustrated in FIG. 3;

PREFERRED MODE FOR CARRYING OUT THE INVENTION

A most preferred mode for carrying out the present invention is described below with reference to the drawings, etc.

EMBODIMENT

Figure 1:
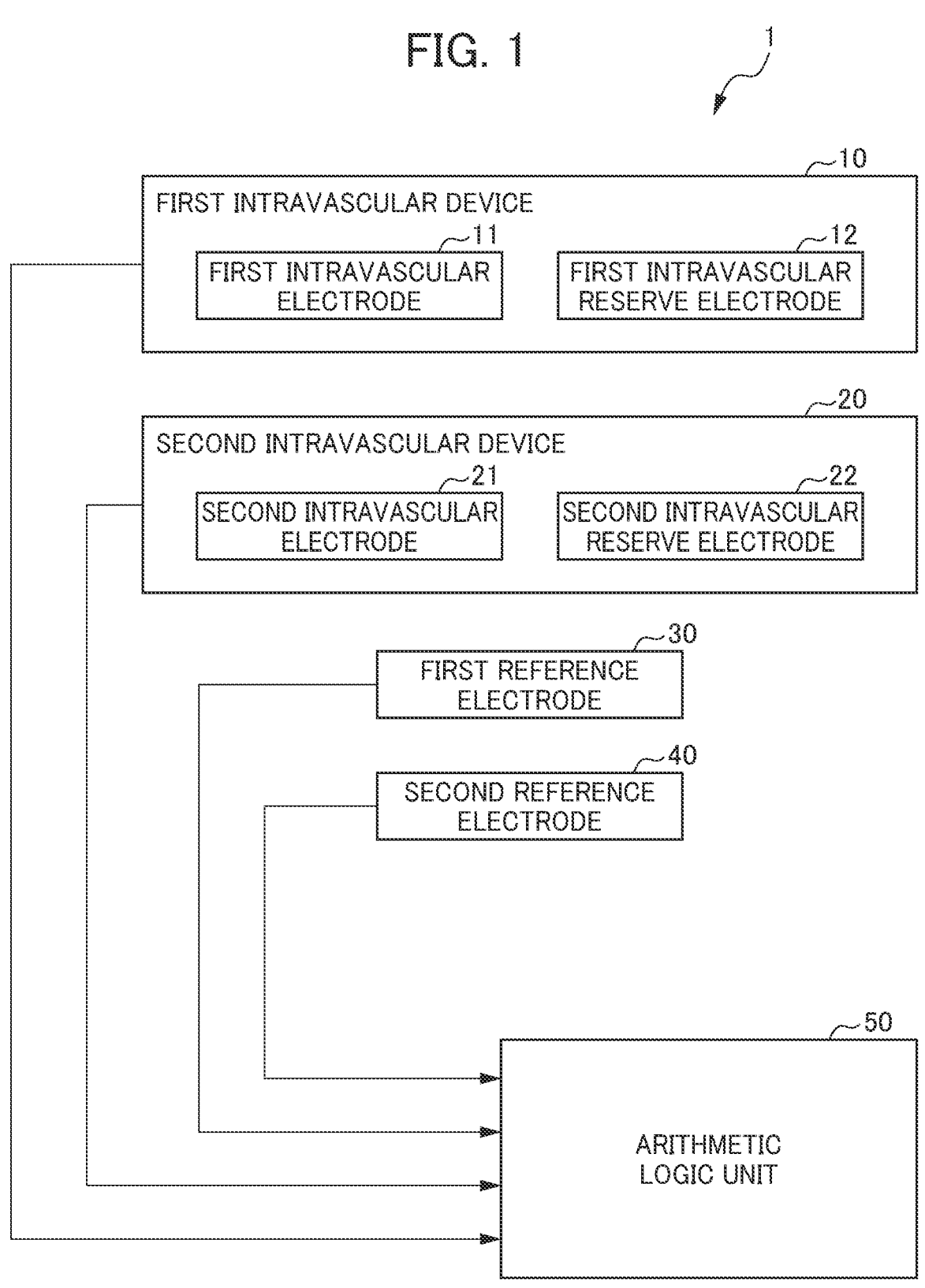
FIG. 1 is a block diagram illustrating the configuration of an embodiment of an apparatus according to the present invention.

FIG. 1 is a block diagram illustrating the configuration of a brain wave measuring apparatus used in a brain wave measuring method according to the present invention. The drawings indicated below, including FIG. 1, are schematic drawings, and in order to facilitate understanding, the sizes and shapes of the components may be illustrated in an exaggerated manner, or may be omitted. In the below description, specific numbers, shapes, materials, and the like are indicated, but these may be modified as appropriate.

An apparatus 1 according to the present embodiment is an apparatus used for detecting or stimulating neural activity of an organism such as an animal or a human. The apparatus 1 includes a first intravascular device 10, a second intravascular device 20, a first reference electrode 30, a second reference electrode 40, and an arithmetic logic unit 50. It should be noted that the present invention is not so limited, and that the number of intravascular devices and reference electrodes may be one, or a plurality of three or more. Alternatively, the reference electrodes and the arithmetic logic unit may be omitted from the apparatus (particularly when used for stimulation).

The first intravascular device 10 is disposed inside a blood vessel (typically a cerebral blood vessel) of an organism during measuring, and includes at least one electrode for detecting or stimulating activity of nerve tissue positioned outside the blood vessel nearby. The electrode is provided on a wire member. The wire member of the present invention refers to a member that is rod-shaped in an extended state, and, unlike a cylinder, does not have an internal space.

FIG. 2 illustrates an example of a configuration of the vicinity of a tip on the side of the first intravascular device 10 to be inserted into a cerebral blood vessel. The first intravascular device 10 is inserted into the cerebral blood vessel through a catheter that is used in conventional cerebral endovascular surgery. At this time, because the electrode is provided on a wire member, the expansive force is smaller compared to a stent, and the wire member has excellent sliding properties with respect to the catheter, and is thus easy to deliver to the cerebral blood vessel. In addition, contact between the wire member and the blood vessel is inhibited (particularly, a wire member that has a rod-shape in a natural state as in the present embodiment barely contacts the blood vessel wall), and therefore, adverse events are unlikely to occur even when the wire member remains for a prolonged time. Therefore, it is preferable that the wire member remains in the blood vessel for one day or longer (specifically, two days or longer, five days or longer, seven days or longer, two weeks or longer, or one month or longer). The first intravascular device 10 includes a core material 13 and an insulator 14. More specifically, the device may be configured as a base in which, for example, an ultrathin wire made of stainless steel as the core material 13, and the outer circumference of the core material 13 is covered by the insulator 14. Examples of the ultrathin wire made of stainless steel for the core material 13 include, for example, a wire made of SUS304 having a diameter of about 0.34 mm. Examples of the insulator 14 include, for example, a polyamide tube or a PTFE tube, or the like. The insulator 14 itself is a cylindrical body, but the inside thereof is filled with the core material, and thus the insulator is considered a wire member in the first intravascular device.

The first intravascular device 10 includes a first intravascular electrode 11 and a first intravascular reserve electrode 12, which are provided on the same wire member spaced apart from each other by less than 1 cm. It should be noted that the present invention is not so limited, and that the number of electrodes provided to one intravascular device may be one, or a plurality of three or more.

In the present embodiment, the first intravascular electrode 11 is provided in a ring shape around the entire circumference with a width of 1 mm, not covered by the insulator 14. The first intravascular electrode 11 is electrically connected to the arithmetic logic unit 50 described below by a wiring 15 passing through the inside of the insulator 14. The first intravascular reserve electrode 12 is disposed at a position 5 mm away from the first intravascular electrode 11. The first intravascular reserve electrode 12 is provided in a ring shape around the entire circumference with a width of 1 mm, not covered by the insulator 14. The first intravascular reserve electrode 12 is electrically connected to the arithmetic logic unit 50 described below by a wiring 16 passing through the inside of the insulator 14. In this way, the first intravascular reserve electrode 12 has a similar configuration to that of the first intravascular electrode 11, and because the electrodes are spaced apart from each other by less than 1 cm and are considered to be able to detect or stimulate the same nerve tissue, the first intravascular reserve electrode serves as a backup to the first intravascular electrode 11.

FIG. 3 illustrates another example of the configuration of the vicinity of the tip on the side of the first intravascular device 10 to be inserted into a cerebral blood vessel. The wire member has a spiral portion 13, the diameter of which can expand and contract circumferentially so as to be retained against the wall of the blood vessel in an expanded state. By retaining the spiral portion 13 against the wall of the blood vessel, the positions of the electrodes 11 and 12 in the blood vessel are essentially fixed, and therefore, activity of nerve tissue can be more precisely detected or stimulated. Because cerebral blood vessels (particularly the cerebral venous sinus) have irregular shapes unlike normal blood vessels, which have nearly circular cross-sections, a spiral body having excellent conforming deformability can achieve both a small expansive force and a position-fixing effect more easily than a rigid stent. This results in a synergistic effect in that, compared with a stent, it is easier to design a smaller contact area with the blood vessel, and to improve delivery performance due to the excellent slidability with respect to the catheter.

The second intravascular device 20 includes a second intravascular electrode 21, a second intravascular reserve electrode 22, a core material 23, an insulator 24, a wiring 25, and a wiring 26. The second intravascular device 20, has the same configuration as the first intravascular device 10 described above, so a detailed description thereof is omitted. It should be noted that the present invention is not so limited, and that it is possible for only one of the first intravascular device or the second intravascular device to have the configuration described above.

In FIG. 3, the electrodes are provided at a location that is not the spiral portion 13 (for example, at the straight portion on the proximal side of the spiral portion 13). However, the present invention is not so limited, and, for example, the electrodes 17 may be provided on the spiral portion as in FIG. 4, or the electrodes may be provided both on the spiral portion 13 and at a location other than the spiral portion 13. The electrodes 11, 12 provided at a location other than the spiral portion experience no change in distance between the electrodes, and are thus favorable in that detection or stimulation of activity of nerve tissue can easily be performed as expected. The electrodes 17 provided on the spiral portion are disposed in contact with or in the vicinity of the blood vessel wall, and are thus favorable in that the sensitivity of the detection or the stimulation of activity of nerve tissue can be easily increased.

The first reference electrode 30 is an electrode for obtaining a reference potential of the brain waves measured by the first intravascular electrode 11 and the first intravascular reserve electrode 12. The first reference electrode 30 is not inserted into the body, but is attached to the outside of the body, for example to an earlobe or the like.

The second reference electrode 40 is an electrode for obtaining a reference potential of the brain waves measured by the second intravascular electrode 21 and the second intravascular reserve electrode 22. The second reference electrode 40 is not inserted into the body, but is attached to the outside of the body, for example to an earlobe or the like.

The arithmetic logic unit 50 acquires the potential information obtained from the above electrodes and calculates a measured result of the brain waves. An example of the simplest form of calculation by the arithmetic logic unit 50 includes, for example, using the measured result from the first intravascular electrode 11 as the measured result of the brain waves, while using the reference potential obtained by the first reference electrode 30 as a reference (zero). In addition to the above, the arithmetic logic unit 50 may perform various types of filter operations, such as noise removal and the like.

Figure 5:
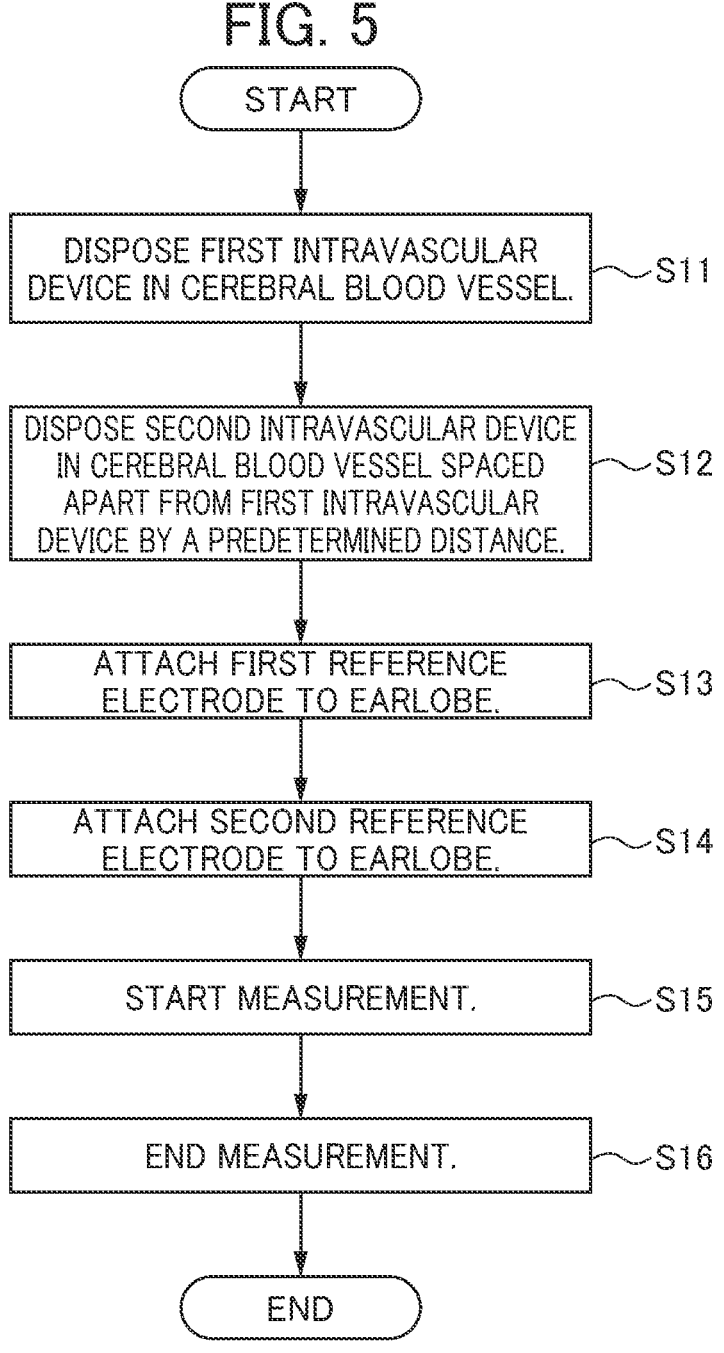
FIG. 5 is a flowchart describing an embodiment of a brain wave measuring method.

Next, a brain wave measuring (nerve tissue activity detection) method using the apparatus 1 according to the present embodiment is described. FIG. 5 is a flowchart describing the brain wave measuring method. In the brain wave measuring method using the apparatus 1 according to the present embodiment, at Step (hereafter abbreviated as S) 11, the first intravascular device 10 is disposed in a cerebral blood vessel.

At S12, the second intravascular device 20 is disposed in a cerebral blood vessel spaced apart from the first intravascular device 10 by a predetermined distance. The cerebral blood vessel may be a venous sinus (for example, the superior sagittal sinus, the sigmoid sinuses, the transverse sinuses, the straight sinus, or the inferior sagittal sinus), cerebral veins such as the internal jugular vein, the cortex veins, and the internal cerebral veins, or cerebral arteries such as the anterior cerebral artery, the middle cerebral artery, or the posterior cerebral artery. For example, when the first intravascular device 10 is disposed on the left hemisphere side, the second intravascular device 20 is disposed on the right hemisphere side. Here, the predetermined distance is preferably a state of being spaced apart by 1 cm or more, and more preferably a state of being spaced apart by 2 cm or more. This is because when the first intravascular device 10 and the second intravascular device 20 are too close to each other, it cannot be distinguished at which position activity is being detected or stimulated.

The method for inserting the first intravascular device 10 and the second intravascular device 20 into the cerebral blood vessels may be the same as a conventionally known cerebral intravascular procedure using a catheter.

At S13, the first reference electrode 30 is attached to an earlobe. At S14, the second reference electrode 40 is attached to an earlobe. At S15, measurement of brain waves is started. At S16, measurement is ended after the required brain wave measurement has been performed.

Next, an experiment verifying that the brain wave measuring method using the apparatus 1 according to the present embodiment allows for appropriate measuring of brain waves is described. In addition to the brain wave measuring method according to the present embodiment, a conventionally used brain wave measuring method, in which electrodes are attached to the surface of the scalp (hereafter referred to as the "comparative example") was performed for the sake of verification. Regarding the brain wave measuring method according to the present embodiment, measuring was performed with the first intravascular electrode 11 disposed at a position in the superior sagittal sinus (the blood vessel extending to the front and back at the center of the brain) near the frontal region of the head. In addition, for the sake of comparison, measurement was performed with an electrode for comparison attached to a position spaced apart from the position in which the first intravascular electrode 11 was disposed.

Figure 6:
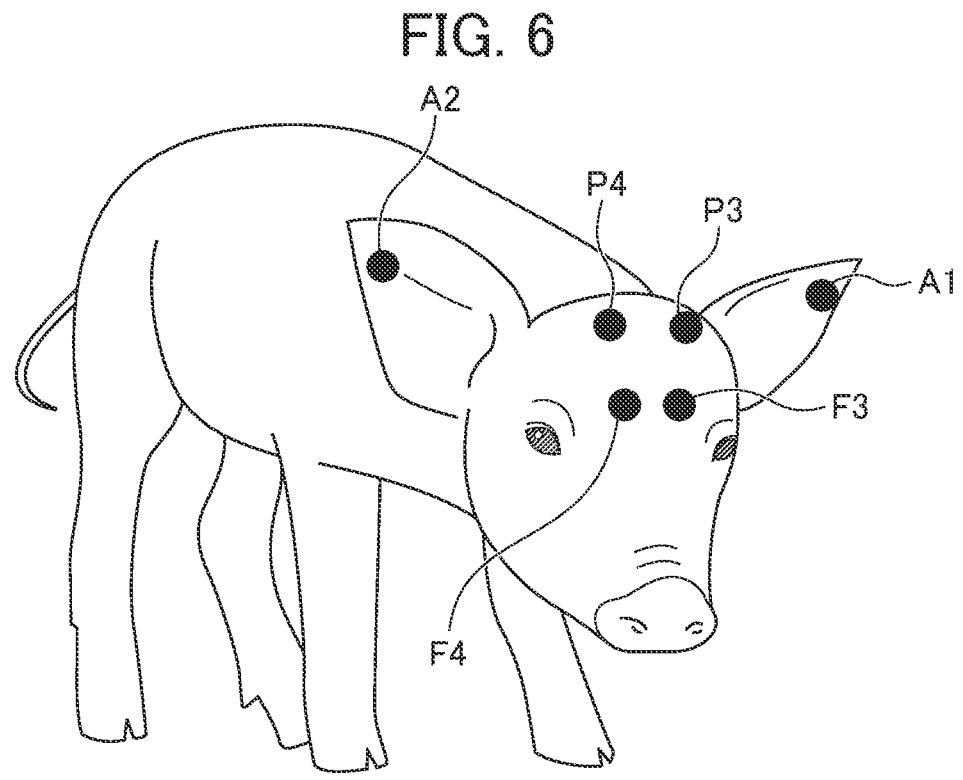
FIG. 6 illustrates measuring locations used in a verification experiment.

FIG. 6 illustrates measuring locations used in the verification experiment. More specifically, in the verification experiment, the brain waves of a pig were measured, and the electrodes for comparison were attached to four locations, namely the frontal region F3 of the left hemisphere, the occipital region P3 of the left hemisphere, the frontal region F4 of the right hemisphere, and the occipital region P4 of the right hemisphere. In addition, a reference electrode for the left hemisphere was attached to the left earlobe A1, and a reference electrode for the right hemisphere was attached to the right earlobe A2. Meanwhile, the first intravascular device 10 according to the present embodiment was disposed with the tip (the first intravascular electrode 11 and the first intravascular reserve electrode 12) thereof being at a location in the superior sagittal sinus nearby the frontal region F3.

Figure 7:
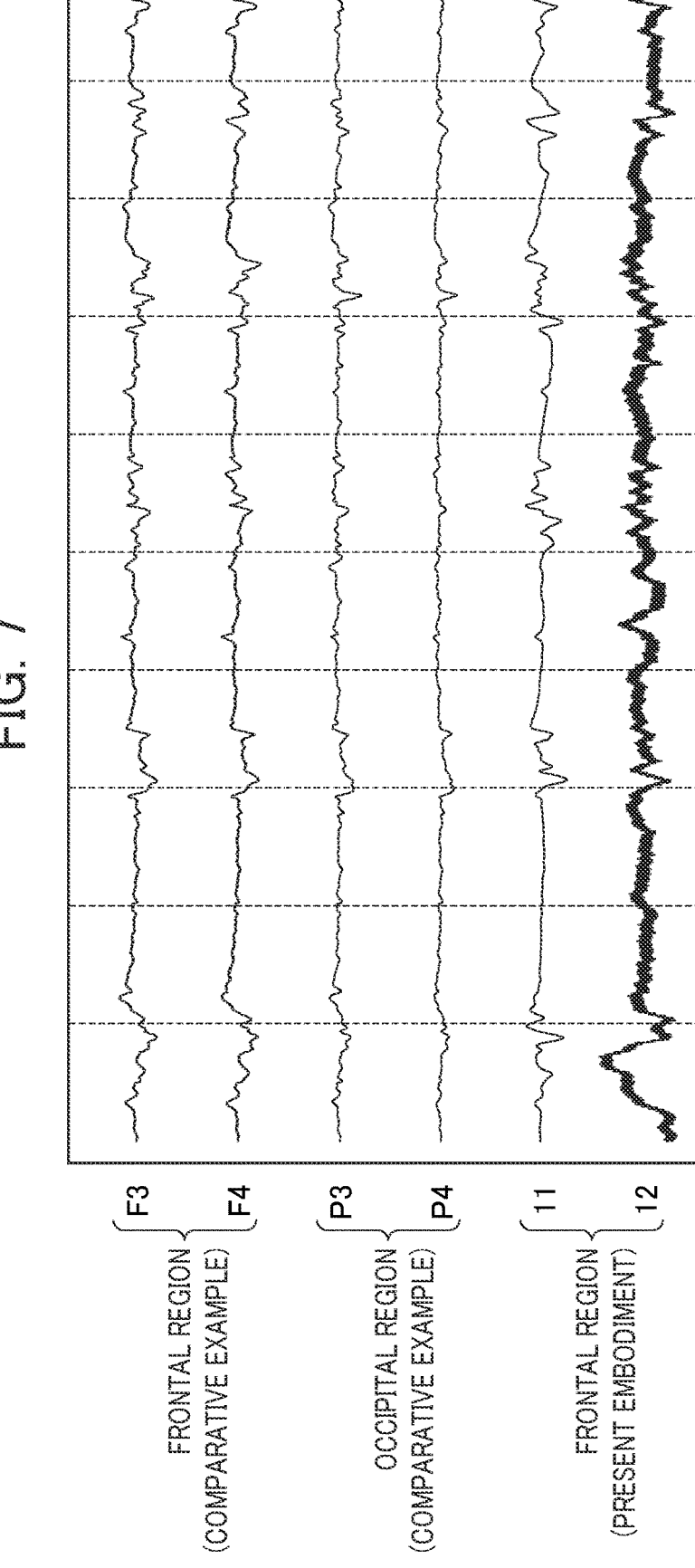
FIG. 7 illustrates part of a measurement result of brain waves obtained in the verification experiment.

FIG. 7 part of a measurement result of brain waves obtained in the verification experiment. F3 is a brain wave obtained from the electrode attached to the frontal region F3 of the left hemisphere in the comparative example. F4 is a brain wave obtained from the electrode attached to the frontal region F4 of the right hemisphere in the comparative example. P3 is a brain wave obtained from the electrode attached to the occipital region P3 of the left hemisphere in the comparative example. P4 is a brain wave obtained from the electrode attached to the occipital region P4 of the right hemisphere in the comparative example. 11 is a brain wave obtained from the first intravascular electrode 11 according to the present embodiment. 12 is a brain wave obtained from the first intravascular reserve electrode 12 according to the present embodiment. It should be noted that the waveforms of 11 and 12 are displayed with the vertical axis direction reduced to a scale of ¼ of the waveforms of the comparative example. From the results illustrated in FIG. 7, the brain waves (11, 12) obtained by the brain wave measuring method according to the present embodiment both include unique peaks with a high sensitivity in the brain waves (F3, F4) obtained by measurement at the frontal region in the comparative example, but do not include unique peaks in the brain waves (P3, P4) obtained by measurement at the occipital region in the comparative example. Conversely, unique peaks of the left hemisphere (F3) and the right hemisphere (F4) are both included in the brain waves (11, 12). The following conclusion can be drawn from these facts. An electrode provided on a wire member is capable of detecting activity of nerve tissue positioned outside the blood vessel nearby with high sensitivity. In addition, detection being possible means that the nerve tissue and the electrode are electrically connected, and therefore, by providing electricity to the electrode from an electric power source, it is also possible to stimulate neural activity with high efficiency. When the difference in distance from the nerve tissue to each of a plurality of electrodes is less than 1 cm, the same brain wave is observed. Therefore, an electrode that is used as a backup to another electrode should be used while being spaced apart by less than 1 cm. When the distance from the nerve tissue to the electrode differs by 1 cm or more, the activity of the nerve tissue having the shorter distance could be distinguished and detected. Therefore, when distinguishing between the activity of a plurality of nerve tissue sites for detection or stimulation, the electrodes should be disposed spaced apart from each other by 1 cm or more.

Based on the above, the present invention can be used for a variety of different purposes. For example, by disposing the intravascular devices according to the present invention in an appropriate manner at locations in cerebral blood vessels nearby the left hemisphere and the right hemisphere and detecting brain waves, the present invention may be used to identify epilepsy foci or detect epileptic seizures. In addition, with regards to disorders that have their causes in the deep portions of the brain (such as epilepsy, depression, involuntary movement due to Parkinson's disease, persistent vegetative state, and the like), the present invention may be used to treat such disorders by disposing the intravascular devices according to the present invention in an appropriate manner with respect to the portions causing the disorder, and providing electrical stimulation.

(Variant)

The present invention is not limited to the embodiment described above, and various variations and modifications are possible without departing from the scope of the present invention.

(1) In the embodiment, an example in which electrodes were disposed at two locations in cerebral blood vessels was described. The present invention is not so limited, and it is possible to dispose three or more electrodes.

(2) In the embodiment, a specific example involving a pig was described. The present invention is not so limited, and the apparatus according to the present invention may be used on mammals such as, for example, mice, rats, monkeys, and humans.

Various embodiments and variants may be used in combination, as appropriate, but detailed description thereof is omitted. In addition, the present invention is not limited by the embodiments described above.

EXPLANATION OF REFERENCE NUMERALS

1 Apparatus
10 First intravascular device
11 First intravascular electrode
12 First intravascular reserve electrode
13 Core material
14 Insulator
15, 16 Wiring
20 Second intravascular device
21 Second intravascular electrode
22 Second intravascular reserve electrode
23 Core material
24 Insulator 25, 26 Wiring
30 First reference electrode
40 Second reference electrode
50 Arithmetic logic unit

The invention claimed is:

1. A method comprising:
disposing, in a cerebral blood vessel of an organism, an intravascular device including at least one electrode provided on a wire member; and
detecting activity of nerve tissue or stimulating of the nerve tissue with the electrode, the nerve tissue being positioned outside the blood vessel near the electrode,
wherein the wire member is formed from a single metal wire and an insulator covering the single metal wire, and
the electrode is provided in a ring shape around an entire circumference of the wire member, not covered by the insulator.

2. The method according to claim 1, wherein
the intravascular device is a single intravascular device or comprises a plurality of intravascular devices, and at least one of the intravascular devices has a plurality of the electrodes, and
the plurality of electrodes are provided on the same wire member and are spaced apart from each other by less than 1 cm.

3. The method according to claim 1, wherein the intravascular device comprises a plurality of intravascular devices, and the method further comprises:
using the plurality of intravascular devices, and
using electrodes included in the respective intravascular devices in such a manner that the electrodes are disposed in the blood vessel and are spaced apart from each other by 1 cm or more.

4. The method according to claim 1, wherein the wire member is expandable and contractable circumferentially, and includes a spiral portion, and the method further comprises:
retaining the spiral portion against a wall of the blood vessel in an expanded state.

5. The method according to claim 1, further comprising:
allowing the intravascular device to remain in the blood vessel for one day or longer.

6. The method according to claim 1, further comprising:
disposing the intravascular device in a cerebral venous sinus as the blood vessel.

7. The method according to claim 1, wherein the electrode is provided at a straight portion of the wire member.

8. A method comprising:
disposing, in a cerebral blood vessel of an organism, an intravascular device including at least one electrode provided on a wire member; and
detecting activity of nerve tissue or stimulating of the nerve tissue with the electrode, the nerve tissue being positioned outside the blood vessel near the electrode,
wherein the wire member is formed from a single metal wire and an insulator covering the single metal wire.

9. The method according to claim 8, wherein the electrode is provided at a straight portion of the wire member.

10. A method comprising:
disposing, in a cerebral blood vessel of an organism, an intravascular device including at least one electrode provided on a wire member; and
detecting activity of nerve tissue or stimulating of the nerve tissue with the electrode, the nerve tissue being positioned outside the blood vessel near the electrode, wherein the wire member is formed from a single metal wire and an insulator covering the single metal wire, and the electrode is provided both at a straight portion and a spiral portion of the wire member.

* * * * *